United States Patent [19]

Burger et al.

[11] Patent Number: 4,928,527

[45] Date of Patent: May 29, 1990

[54] METHOD AND DEVICE FOR NONDESTRUCTIVE EVALUATION

[75] Inventors: Christian P. Burger, College Station, Tex.; Thomas D. Dudderar, Chatham, N.J.; John A. Gilbert; Bruce R. Peters, both of Huntsville, Ala.; James A. Smith, Idaho Falls, Id.

[73] Assignee: AT&T Bell Laboratories, Murray Hill, N.J.

[21] Appl. No.: 187,805

[22] Filed: Apr. 29, 1988

[51] Int. Cl.⁵ ............................................. G01N 29/00
[52] U.S. Cl. ...................................... 73/657; 356/358
[58] Field of Search ........................ 73/657, 655, 659; 356/349, 356, 355, 357, 345, 358

[56] References Cited

U.S. PATENT DOCUMENTS

| | | | |
|---|---|---|---|
| 4,381,676 | 5/1983 | Kaule et al. | 73/657 |
| 4,572,949 | 2/1986 | Bowers et al. | 73/657 |
| 4,619,529 | 10/1986 | Iuchi et al. | 73/657 |
| 4,652,744 | 3/1986 | Bowers et al. | 73/657 |
| 4,723,448 | 2/1988 | Veligdan | 73/657 |
| 4,824,251 | 4/1989 | Slotwinski et al. | 356/358 |

OTHER PUBLICATIONS

Non-Destructive Testing, MacDonald & Evans LTD, 1959, J. F. Hinsley.
Prentice-Hall Inc., 1962, Ultrasonic Flaw Detection in Metals, B. Banks et al.
Materials Evaluation, vol. 38 (Jan. 1980), No. 1, pp. 86-91, "Noncontact Material Testing Using Laser Energy Deposition and Interferometry", C. A. Calder et al.
Journal of Nondestructive Evaluation, vol. 7, No. 1 (1987), pp. 57-64, "Laser Excitation Through Fiber Optics in NDE", C. P. Burger et al.
Rev. Sci. Instrum. 55 (2), Feb. 1984, "Fiber-Optic Interferometer for Remote Subangstrom Vibration Measurement", A. D. Drake et al.

Primary Examiner—Michael J. Tokar
Assistant Examiner—Louis M. Arana
Attorney, Agent, or Firm—Peter A. Businger

[57] ABSTRACT

Ultrasonic surface examination, of interest in a variety of manufacturing and maintenance situations, is facilitated by a method which involves localized sensing of a surface wave by optical-fiber interferometry. The method is particularly applicable for examination of surfaces in confined spaces and wherever line-of-sight examination is difficult.

16 Claims, 2 Drawing Sheets

METHOD AND DEVICE FOR NONDESTRUCTIVE EVALUATION

TECHNICAL FIELD

The invention is concerned with the evaluation of physical objects and, more specifically, with nondestructive testing and evaluation.

BACKGROUND OF THE INVENTION

As reviewed, e.g., by J. F. Hinsley, *Non-destructive Testing*, Macdonald & Evans, 1959, the field of nondestructive testing and evaluation includes a variety of methods as based on physical effects such as, e.g., radiological, acoustic, and magnetic interactions with test objects. More specifically, and as particularly germane to the invention, acoustic or ultrasonic methods involve the monitoring of an elastic wave as influenced by flaws or inhomogeneities in a test object; see, e.g., B. Banks, *Ultrasonic Flaw Detection in Metals*, Prentice-Hall, 1962.

For testing purposes, an elastic wave may be generated by means of an electro-acoustic transducer based on electromagnetic, electrostatic, magnetostrictive, or piezo-electric effects; also, waves have been generated optically as described, e.g., by C. A. Calder et al., "Noncontact Material Testing Using Laser Energy Deposition and Interferometry", *Materials Evaluation*, Vol. 38 (1980), No. 1, pp. 86-91 (where, also, monitoring by interferometry is described) and by C. P. Burger et al., "Laser Excitation Through Fiber Optics in NDE", *Journal of Nondestructive Evaluation*, Vol. 7 (1987), pp. 57-64, the latter disclosing laser energy as transmitted to a surface of interest via a flexible optical-fiber element.

Monitoring by interferometry involves the use of two coherent beams of light: an object beam which passes through—or is reflected by—an object under observation, and a reference beam which is unaffected by the object. Superposition of the two beams results in interference and, in a wide-aperture (full-field) system, the resulting intensity distribution yields an interferometric fringe pattern representing a contour map of constant optical path or optical phase difference.

While, typically in a laboratory setting, interferometric monitoring can be carried out with line-of-sight radiation, industrial settings may require testing in confined spaces and at hidden surfaces. Accordingly, it is a purpose of the invention to provide for a test device and method for detecting and characterizing flaws, such device and method being particularly suited with respect to ease of access to test objects in commercial practice.

SUMMARY OF THE INVENTION

In the manufacture and maintenance of industrial articles, the invention provides for the evaluation of articles and components with respect to inhomogeneity of a surface property such as, e.g., composition or continuity. In accordance with the invention, energy is applied to a surface of interest (piezoelectrically or optically, for example), and a surface wave (Rayleigh wave) is sensed by optical-fiber interferometry as characterized by the use of at least one optical fiber to transmit a probe signal to a surface point as well as for transmitting returning reference and objects signals. (An optical fiber is understood as comprising a waveguiding core-cladding structure for guiding one or several modes of radiation having a wavelength corresponding to ultraviolet, visible, or infrared radiation.)

Use of optical-fiber interferometry as preferred in accordance with the invention facilitates testing in assembly-line manufacture as well as in the preventive maintenance of critical components and assemblies such as, e.g., jet engines and rocket motors. The method is particularly advantageous for the inspection of otherwise hard to reach surface locations, and such method is advantageous also in that laser radiation used for probing remains fiber-guided over most of the optical path, thereby enhancing industrial safety especially when fiber ends are shielded.

DETAILED DESCRIPTION

Figure 1:
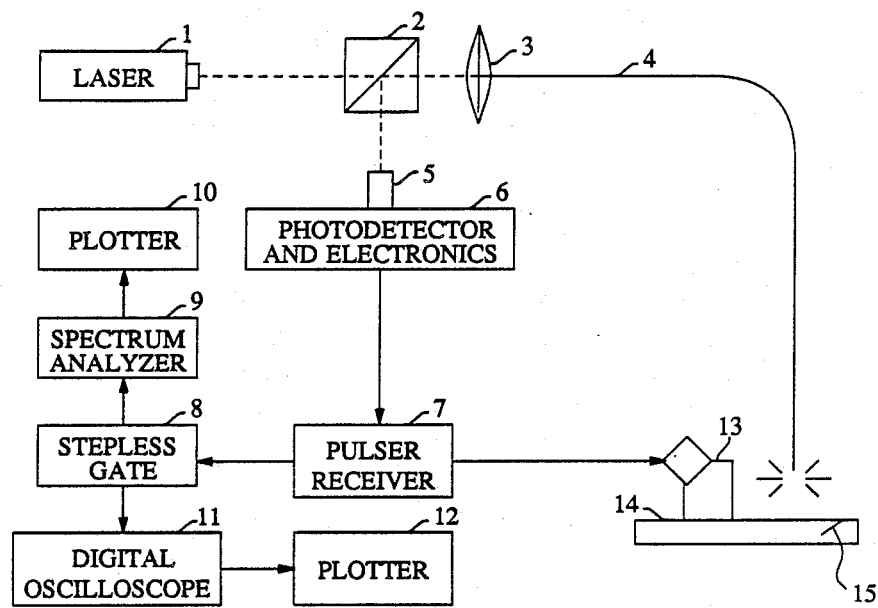
FIG. 1 is a schematic representation of a first device representing a first preferred embodiment of the invention.

FIG. 1 shows laser 1, lens 3, and single-mode optical fiber 4 in optical alignment with a first beam of variable beam splitter 2. Optically aligned with a second beam are multi-mode optical fiber 5 and photodetector 6 with wide-band amplification electronics electrically connected to pulser-receiver 7. The latter is connected, via stepless gate 8, to spectrum analyzer 9 and digital oscilloscope 11 which, in turn, are connected to respective plotters 10 and 12. Pulser-receiver 7 is further connected to piezoelectric transducer 13 which is physically attached to an object 14 to be tested, and the tip of fiber 4 is in proximity of object 14 for interferometric detection of surface waves such as, e.g., waves influenced by an inhomogeneity 15.

Device operation involves splitting of the unspread output from the laser so as to produce two beams having essentially equal intensity. One of the beams is wasted, the other is focused into the single-mode optical fiber. A small percentage of light traveling down the fiber suffers Fresnel or internal reflection from the output end and serves as the reference wave. The remainder of the light emerges from the fiber and is scattered by the diffusely reflecting surface of the test object. A small, detectable fraction of the scattered light is reflected back into the optical fiber as return object wave to join and interfere with the internally reflected reference wave in its propagation back through the fiber. Upon exiting from the optical fiber, the returning light is collimated by the focusing lens, and deflected by the beam splitter so that approximately half of the returning light is passed into the multimode fiber. Typically, such a fiber has a core diameter on the order of 50 micrometers as is advantageous in the interest of low-loss coupling; with low-intensity signals, an additional lens may be used for light insertion into the multimode fiber.

Since the optical-fiber interferometer is excited by coherent light, there will be destructive interference whenever the optical path length of the externally reflected and recaptured light beam differs from the optical path length of the internally reflected reference beam by (an odd multiple of) a half wavelength. This difference is due to travel of externally reflected light back and forth across the gap or Fizeau cavity between the fiber tip and test surface. On the other hand, if this difference is (a multiple of) a whole wavelength, interference will be constructive. Thus, if the intensities and polarizations of the two reflections are approximately equal, the light traveling back along the fiber will be seen to brighten and darken as the reflecting test surface moves towards or away from the optical fiber tip. A displacement-induced change in cavity length of just one quarter of an optical wavelength is sufficient to shift the output signal intensity from a maximum to a minimum or vice versa.

One important feature of an optical-fiber interferometer is intrinsic self-alignment of reference and object beams; furthermore, throughout most of the interferometer both beams experience the same environment of temperature, pressure, vibration, etc. Alignment is critical, however, with respect to coupling of light into the fiber and separating out the returning signal. For the sake of maximizing contrast in the returned signal, a translation stage may be used to move the fiber tip in and out from the specimen surface. Also, for the sake of enhancing the intensity of the externally reflected signal e.g. in the case of a low-reflecting test surface, a compact objective or rod lens may be added to the fiber tip to collimate the light. Acceptable results were obtained without such additional lens on a moderately reflective machined steel surface, with fiber tip standoff distance of up to 1 cm.

A test arrangement as schematically shown in FIG. 1 was used to examine, as a test object, a steel bar measuring 25.4 by 25.4 by 254 mm, with an oblique slot machined to a depth of 2 mm from the surface and having a length of 2.8 mm. When the machined "flaw" was located between the piezoelectric transducer and the optical fiber tip, the delay or time of flight of the Rayleigh wave observed in the oscilloscope trace was seen to decrease as the fiber tip was translated towards the flaw. As the fiber tip moved past the flaw in the direction of the point of excitation (see FIG. 1), the signal increased markedly in amplitude and, moreover, several additional signals appeared—ostensibly as associated with components of the wave that had been reflected from the flaw. Such in-line input and reflected waves are very difficult, if not impossible, to detect by means of conventional contact transducers. Indeed, none were observed in piezoelectric pitch-catch tests as carried out with the steel bar.

The time-domain display of the ungated optical-fiber interferometer signal transmitted to the oscilloscope through a high-pass ($>1$ MHz) filter showed spikes which were readily identified as corresponding to the Rayleigh wave generated by the piezoelectric transducer and to the partially reflected wave from the machined surface flaw: since reflected waves are monitored in-line, their temporal spacing or time of travel can be used to estimate the location of a flaw. This demonstrates an advantage of optical-fiber interferometry as compared, e.g., with spectrometry using a piezoelectric sensor. Since the former does not involve the attachment of an energy-absorbing mass to the surface at the point of measurement, the acoustic wave is not altered by the sensor, so that it becomes possible to monitor input and reflected waves together.

By processing the signals through the stepless gate to the spectrum analyzer instead of the oscilloscope, frequency-domain information was obtained. Strongest reflected frequencies were found to lie near 1.5 MHz, corresponding to a wavelength of slightly less than 2 mm - approximately the depth of the flaw. Also, significant attenuation was found in the reflected-wave spectrum near 0.95 MHz, corresponding to a wavelength of approximately 3 mm—close to the 2.8-mm length of the flaw.

Figure 2:
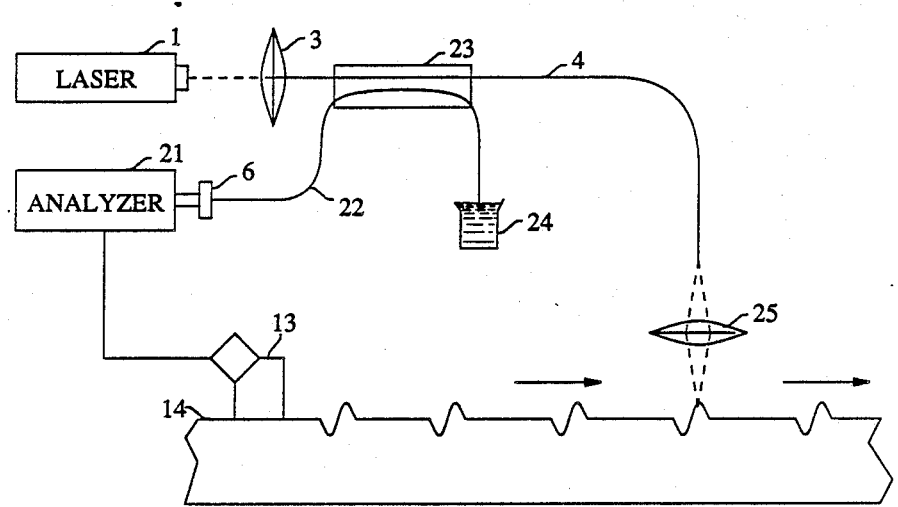
FIG. 2 is a schematic representation of a second device representing a second preferred embodiment of the invention.

A difficulty which may arise in the use of the arrangement of FIG. 1 lies with the separation of the return signal from the input-end reflection, and FIG. 2 shows a modified arrangement which readily ensures such separation. Specifically, FIG. 2 shows laser 1, objective lens 3, single mode optical fiber 4, photodetector 6 connected to analyzer 21 (comprising e.g., components 7–12 of FIG. 1), ultrasonic transducer 13, test object 14, optical fiber 22, half-power or 3dB coupler 23, and optical termination 24, e.g., in the form of a reservoir of index-matching fluid. Also, an additional objection lens 25 is shown between the tip of fiber 4 and the test object 14.

As in any half-fringe interferometer used to achieve high resolution, maximum sensitivity and linear range are achieved with the cavity or stand-off distance set to yield a single mid-way between the highest and lowest intensities. At these extremes, which lie a quarter wavelength apart, the sensitivity is zero. Thus, disturbances such as, e.g., thermal expansion and low-frequency mechanical vibrations, by altering the spacing of the fiber tip from the test surface, can shift the sensitivity from its maximum to nothing. While low-frequency ($<1$ MHz) vibrations having amplitudes significantly less than one-eighth wavelength can easily be filtered out of the signal electronically, this is not the case for largeramplitude disturbances.

Figure 3:
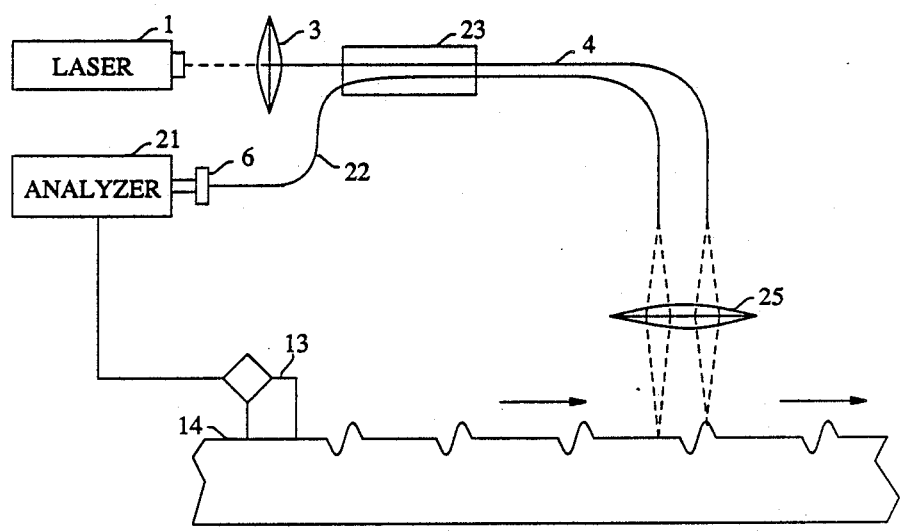
FIG. 3 is a schematic representation of a third device representing a third preferred embodiment of the invention.

One possible way of eliminating all long-wavelength, large-amplitude mechanical noise involves the use of both ends ends of a bidirectional coupler as a paired interference sensor to monitor relative surface motions at two points slightly more than one acoustic wavelength apart (approximately 3 mm at 1 MHz in steel). This is illustrated by FIG. 3 which shows structure as described above with respect to FIG. 2, except that fiber 22, rather than being optically terminated, serves to feed a return signal to analyzer 21. On the basis of the known relative position of the fiber tips, interpretation of the two return signals can be used to eliminate the influence of mechanical noise.

While experiments as described above involved the use of piezoelectric transducers, the use of other means for wave generation is not precluded. In particular, as disclosed in the paper by C. P. Burger et al. cited above, acoustic waves can be generated by means of pulses of laser light guided through a noncontact optical fiber. Moreover, and independent of the type of wave generation used, a scanning mode of operation can be employed as a noncontacting optical-fiber sensor readily can be scanned across even complicated surfaces. And finally, in the interest of enhanced interrogation and data gathering capabilities, such sensors readily can be combined into sensor arrays.

We claim:

1. In the manufacture or maintenance of an article, a method for examining at least a portion of a surface of said article with respect to inhomogeneity of a surface property, said method comprising (i) providing energy to said surface, and (ii) sensing a surface wave at least at a point of said portion, characterized in that sensing of said surface wave comprises fiber-optical interferometry between first and second optical signals here designated as reference and object signals, said reference and object signals being derived from an optical signal here designated as laser signal and having been transmitted by an optical fiber, said first optical signal being derived from said laser signal by internal reflection of a first portion of the power of said laser signal at the end of said optical fiber, and said second optical signal being derived from said laser signal by emission of a second portion of the power of said laser signal from the end of said fiber, followed by reflection from said surface at said point.

2. The method of claim 1 in which said energy is provided by piezoelectric means.

3. The method of claim 1 in which said energy is provided by optical means.

4. The method of claim 3 in which said energy is provided via an optical fiber.

5. The method of claim 1 in which fiber-optical interferometry comprises use of a single-mode fiber.

6. The method of claim 1 in which a lens is used to collimate light at said point.

7. The method of claim 1 in which a bidirectional optical coupler is used to couple radiation returning from said point into an interferometric analyzer.

8. The method of claim 1 in which reference and object signals are transmitted by different optical fibers.

9. A device for examining at least a portion of a surface of an article with respect to inhomogeneity of a surface property, said device comprising (i) first means for providing energy to said surface, and (ii) second means for sensing a surface wave at least at a point of said portion, characterized in that said second means comprises a fiberoptical interferometer comprising a laser, an optical fiber disposed to accept an optical signal from said laser, and analyzing means for interferometrically analyzing first and second optical signals derived from an optical signal transmitted by said fiber and here designated as laser signal, said first optical signal being derived from said laser signal by internal; reflection of a first portion of the power of said laser signal at the end of said optical fiber, and said second optical signal being derived from said laser signal by emission of a second portion of the power of said laser signal from the end of said fiber, followed by reflection from said surface at said point.

10. The device of claim 9 in which said first means comprises a piezoelectric transducer.

11. The device of claim 9 in which said first means comprises a source of electromagnetic radiation.

12. The device of claim 11 in which said first means comprises an optical fiber coupled to said source.

13. The device of claim 9 in which said second means comprises a single-mode fiber.

14. The device of claim 9 in which said second means comprises collimating means.

15. The device of claim 9 in which said second means comprises a bidirectional optical coupler.

16. The device of claim 9 in which said second means comprises two optical fibers.

* * * * *